(12) United States Patent
Popilek et al.

(10) Patent No.: US 7,685,661 B2
(45) Date of Patent: Mar. 30, 2010

(54) FLEXIBLE PAD SUPPORT, SUCH AS ENCLOSING ONE OR MORE SPEAKERS AND PLACEABLE UNDERNEATH A PILLOW FOR PROVIDING A MUFFLED AND SELECTIVELY AUDIBLE ALARM

(76) Inventors: Mark Popilek, 4946 Meniminee La., Clarkston, MI (US) 48348; Margaret Popilek, 4946 Menominee La., Clarkston, MI (US) 48348

( * ) Notice: Subject to any disclaimer, the term of this patent is extended or adjusted under 35 U.S.C. 154(b) by 217 days.

(21) Appl. No.: 11/738,905

(22) Filed: Apr. 23, 2007

(65) Prior Publication Data

US 2007/0253591 A1    Nov. 1, 2007

Related U.S. Application Data

(60) Provisional application No. 60/794,990, filed on Apr. 26, 2006.

(51) Int. Cl.
H04R 5/00    (2006.01)
A47G 9/10    (2006.01)

(52) U.S. Cl. .................. 5/639; 5/904; 381/301; 381/333

(58) Field of Classification Search .......... 5/639, 5/904, 905; 381/301, 333, 388, 87, 332, 381/334, 386, 309, 370
See application file for complete search history.

(56) References Cited

U.S. PATENT DOCUMENTS

| 3,621,155 | A | 11/1971 | Pruitt et al. |
| 3,946,316 | A | 3/1976 | Hough |
| 4,038,499 | A | 7/1977 | Yeaple |
| 4,070,553 | A * | 1/1978 | Hass ............................ 381/301 |
| 4,782,533 | A | 11/1988 | Haynie |
| 4,841,587 | A * | 6/1989 | Carter et al. .................... 5/419 |
| 4,862,438 | A | 8/1989 | Fry |
| 5,109,421 | A * | 4/1992 | Fox ............................ 381/333 |
| 5,123,133 | A | 6/1992 | Albert et al. |
| 5,179,747 | A | 1/1993 | Zink |
| 5,313,678 | A | 5/1994 | Redewill |
| D379,186 | S | 5/1997 | Taylor |
| 5,713,741 | A * | 2/1998 | DeMars ....................... 434/319 |
| 5,865,771 | A * | 2/1999 | Shuto et al. .................... 601/47 |
| 6,044,161 | A | 3/2000 | Lee |
| 6,098,220 | A * | 8/2000 | Momma ......................... 5/636 |
| D481,246 | S | 10/2003 | Peterson |
| 6,668,407 | B1 * | 12/2003 | Reitzel ........................... 5/656 |
| 6,704,958 | B2 | 3/2004 | Gohl |
| D513,282 | S | 12/2005 | Yu et al. |
| 7,093,903 | B2 * | 8/2006 | O'Connor et al. ........... 297/397 |
| 7,380,298 | B2 * | 6/2008 | Hernandez ...................... 5/639 |
| 2007/0160244 | A1 * | 7/2007 | Hedaya ........................ 381/333 |
| 2007/0223760 | A1 * | 9/2007 | Fan ............................. 381/333 |

FOREIGN PATENT DOCUMENTS

GB    2113502 A *    8/1983

* cited by examiner

*Primary Examiner*—Michael Trettel
(74) *Attorney, Agent, or Firm*—Gifford, Krass, Sprinkle, Anderson & Citkowski, P.C.

(57) ABSTRACT

A sound generating device having a flexible three-dimensional and substantially planar shaped body including a soft interior encased within a durable exterior covering. A pair of speakers are arranged within the body at first and second locations proximate an upper facing surface. The padded body is adapted to being placed underneath an existing cushion for delivering an audio output, and which is selectively audible to an individual whose head is supported upon the cushion.

9 Claims, 5 Drawing Sheets

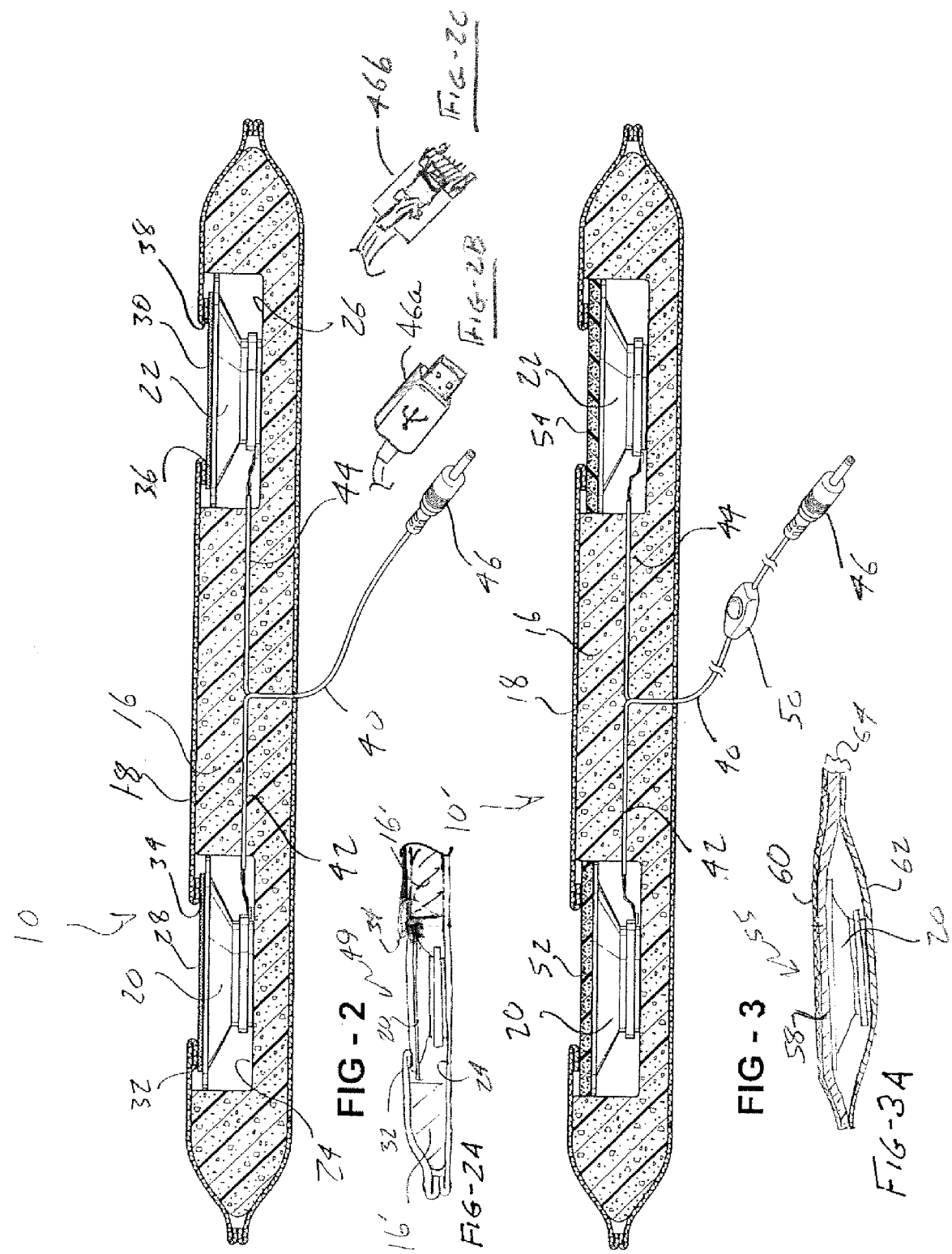

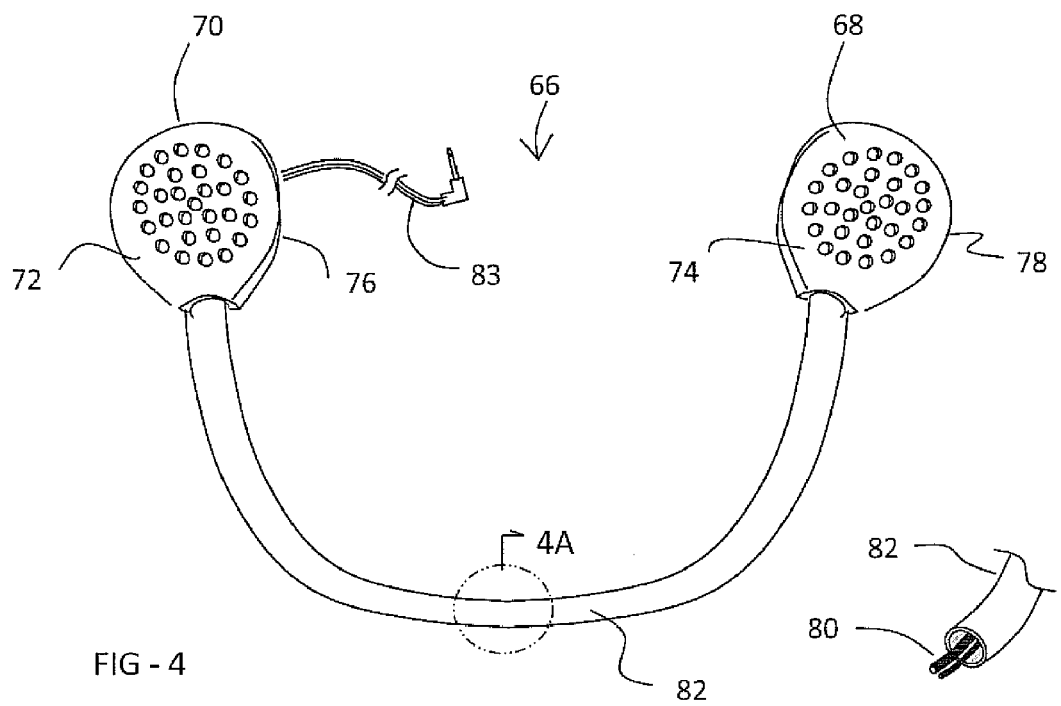
FIG - 4
FIG - 4A
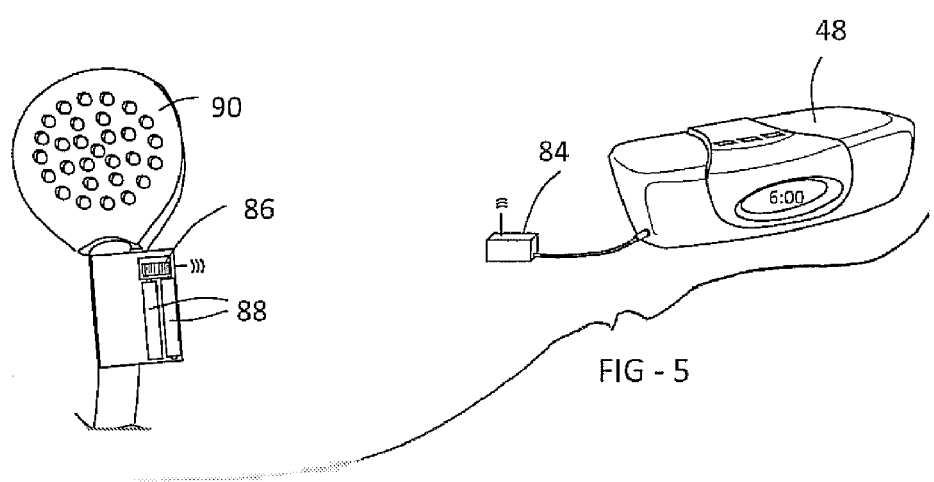
FIG - 5

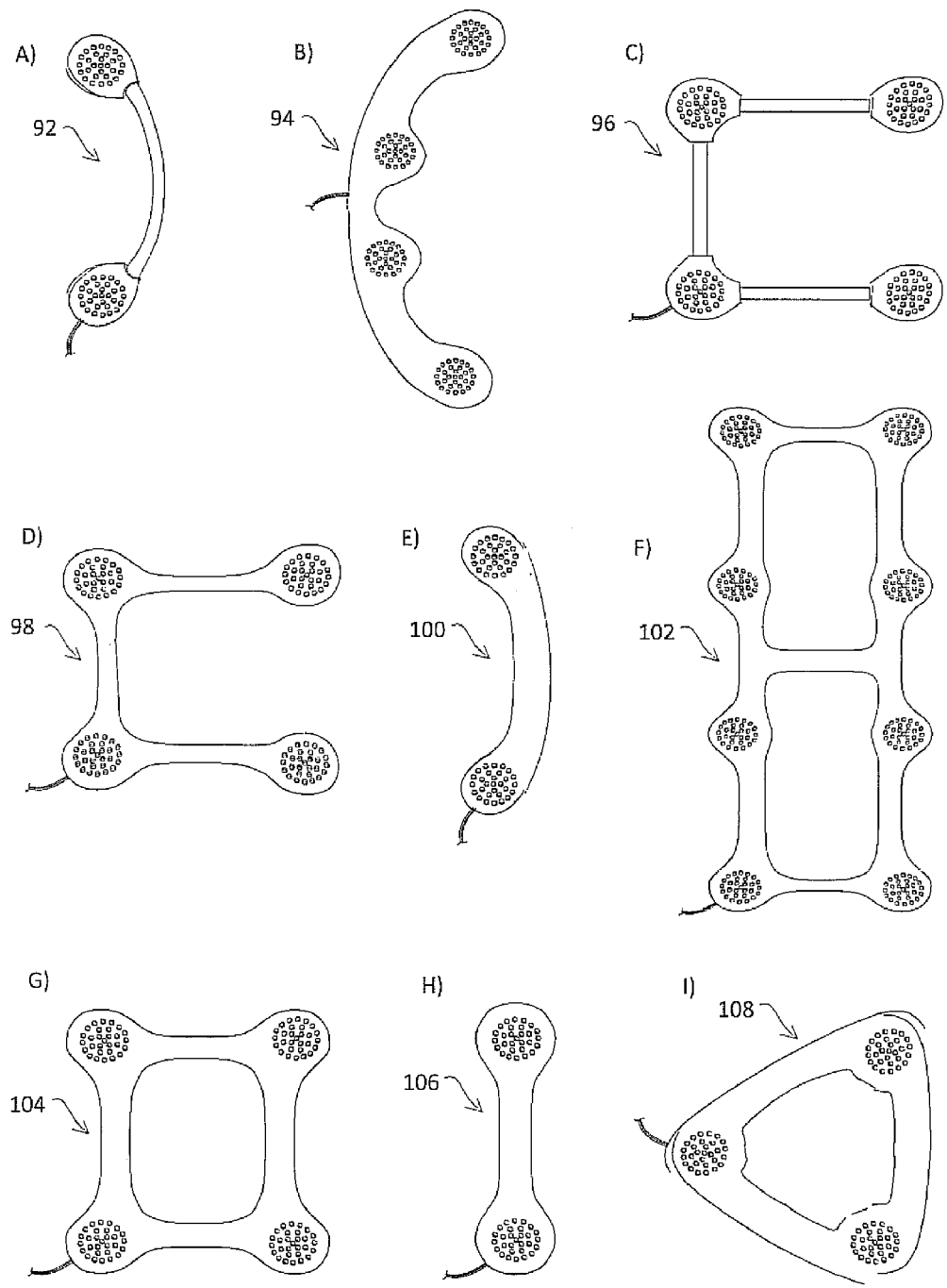

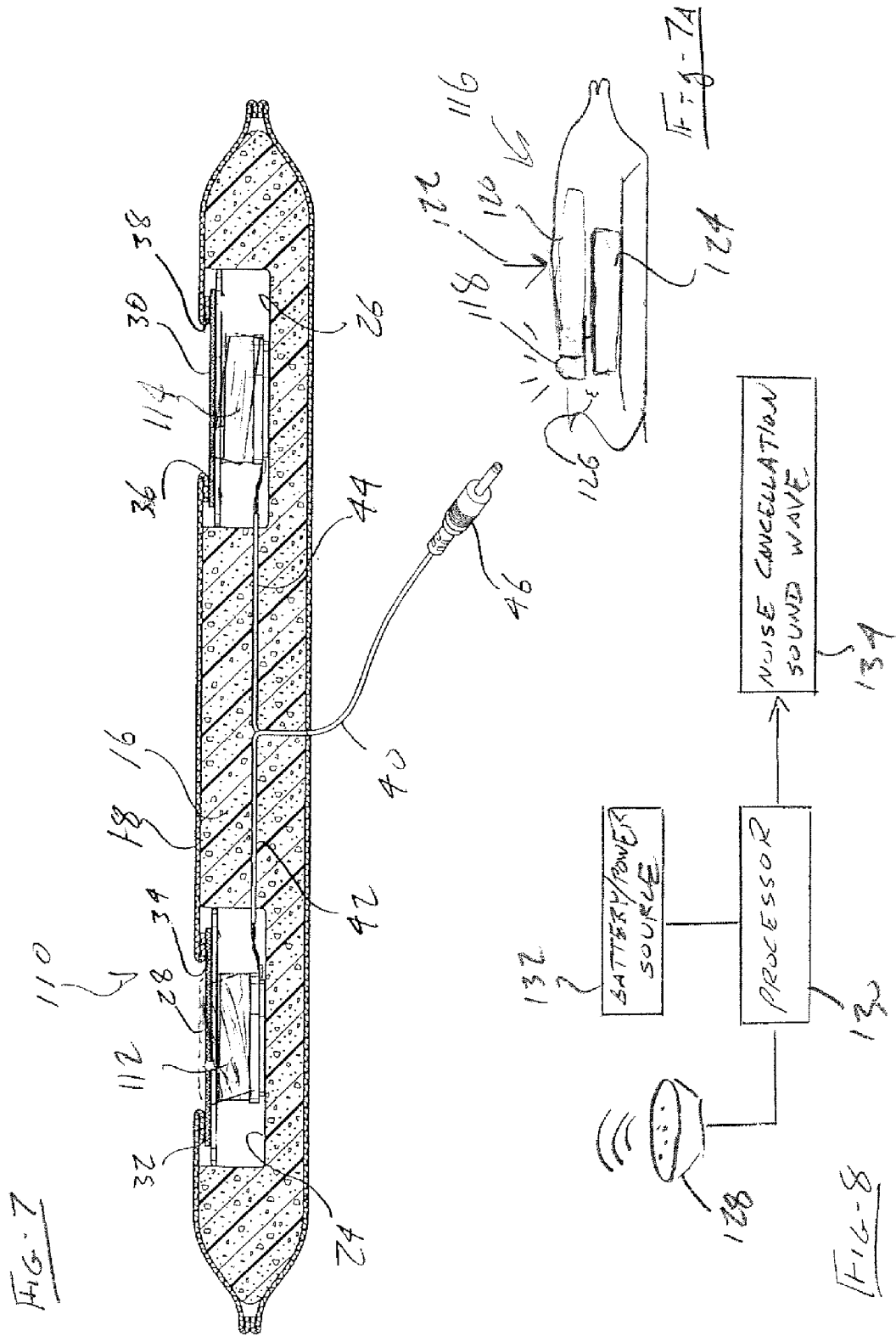

FLEXIBLE PAD SUPPORT, SUCH AS ENCLOSING ONE OR MORE SPEAKERS AND PLACEABLE UNDERNEATH A PILLOW FOR PROVIDING A MUFFLED AND SELECTIVELY AUDIBLE ALARM

CROSS-REFERENCE TO RELATED APPLICATIONS

The present application claims the priority of U.S. Provisional Patent Application Ser. No. 60/794,990. filed Apr. 26, 2006, for "Flexible Pad Support, Such As Enclosing One or More Speakers and Placeable Underneath a Pillow for Providing a Muffled and Selectively Audible Alarm."

BACKGROUND OF THE INVENTION

1. Field of the Invention

The present invention relates generally to an enclosed and supporting audible device, More specifically, the present invention teaches a pad enclosing audible device, by which one or more speakers are incorporated into a flexible and, selectively, cushioning support structure, further such that the pad is capable of being placeable such as underneath a conventional pillow or the like to provide a user selective audible output (i.e., music or the like), as well as a likewise selective alarm.

2. Description of the Prior Art

U.S. Pat. No. 6,704,958, issued to Gohl, teaches a contoured foam body exhibiting underside mounted loudspeakers detachably mounted into corresponding recesses on the underside of the pillow body. The context of this invention is the provision of a therapeutic pillow body constructed of an elastically deformable material and in which several speakers can be positioned along a lengthwise extending rail defined in the pillow, the rail likewise being constructed of an elastically deformable material and capable of being detached from a corresponding recess defined in the pillow underside.

Japanese Patent No. 2021818 (Fumio) is directed to a muffled alarm device, and teaching a self-contained battery powered unit with speakers built into a base frame, upon which a foamed cushioning body is formed. An alarm clock operates on a power supply available from a charge type battery, a cord plug and the like being built into a pillow frame of a material such as a ceramic, plastic or wood. A speaker for the alarm clock device is suitably sized such that a desired number is fitted within the network of frame defined holes positioned underneath the user's head. An overlaying cushion is intended to operate as a headphone, a corresponding sound level being inaudible from a distance.

The device set forth in Fumio also contemplates the provision of a heat escape hole for dissipating thermal buildup resulting from use of the device. That said, Fumio is limited to teaching a combined cushioning pillow, the same being hingedly supported to a substantially rigid base frame constructed of one of ceramic, wood or plastic, and with built in audio alarm clock and speaker for creating a localized sound output.

Zink, U.S. Pat. No. 5,179,747, teaches a pillow including a top and bottom fibrous web defining a casing including a radio mounted within the casing and cooperating with a remotely located speaker. The pillow further includes the speaker mounted within a speaker housing, this including fluid filled walls, and where the housing cavity includes compressed fluid capsules to accommodate the impact to the speaker unit. The pillow structure may further be provided with a serpentine pneumatic chamber filled with further compressible fluid capsules to afford comfort and cushioning to a user, as well as protection to the components of a radio-clock system.

Fry, U.S. Pat. No. 4,862,438, teaches a combination functioning pillow/audio system and in which a substantially rectangularly-shaped pillow casing is filled with stuffing material. An audio signal generating device such as a tape recorder is provided within the pillow casing along with a speaker and a battery for providing audible sound. Switches are provided at the corners of the pillow and are connected to the signal generating device for energizing and deenergizing the same. A battery jack is provided on the pillow casing, for connecting to a piggyback pillow having a speaker located therein, and which also generates audible sound via the signal received through the audio jack and an audio extension cord. A pocket is provided within the pillow casing for housing the various components of the audio system.

U.S. Pat. No. 5,713,741, issued to DeMars, teaches a storybook pillow in which a pillow is designed to rest under the head of a human and including a radio transmitter. Upon the pillow being used by applying pressure to the pillow, and by the user's head, the radio transmitter is activated emitting a signal. A radio receivers separate from the pillow but located in close proximity thereto, picks up the signal and activates a sound playback device which reproduces a recorded sound. The radio receiver is mounted in conjunction with the representation of a book.

Finally, U.S. Pat. No. 4,782,533, issued to Haynie, teaches a stereophonic pillow speaker system and which includes a rectangular foam base member. A pair of stereophonic loudspeakers are mounted within holes in the base member. An inner cushion wrapping is provided around the base member, an outer cushion wrapping being wrapped around the inner cushion wrapping. An electric wire extends from the loudspeakers out of the pillow through one corner thereof and a foam securing member secures the wire to the corner of the pillow. A jack located on the end of the wire can be plugged into a sound source, such as a tape player.

SUMMARY OF THE PRESENT INVENTION

The present invention discloses a sound generating device which is an improvement over prior art devices, particularly in that it is incorporated into a small, relatively flat and flexible pad-like element which is capable of easily being inserted underneath an existing pillow or like cushion. The advantage of a pad-shaped sound generating component is that it permits selective audible (e,g. music/alarm as well as possibly vibratory) output, to a user whose head is supported upon the pillow, and without disturbing a partner of the user.

The invention exhibits a three-dimensional and substantially planar shaped body having a specified shape and size and including a soft (e.g. selectively foam cushioned) interior encased within a durable exterior covering. A pair of speakers are arranged within apertured portions defined in the body, such that the speakers are arrayed in an upper facing direction relative to a surface of the substantially planar shaped body. The exterior covering incorporates an audible permissive portion located over each of the speakers. In use, the padded body is adapted to being placed underneath an existing cushion for delivering an audio output, which is selectively audible to an individual whose head is supported upon the cushion, and further so that the output is not audible to a partner sleeping next to the user, as well as being likewise inaudible at any other location within the selected room enclosure.

Additional features include the exterior covering having a specified thickness and consistency and including at least one of a fabric and a rubberized material. A wire communicates with the sound generating component and extends from the body, terminating in an input jack for connection to an external audible generating device. Other features include an activate/deactivate switch associated with an intermediate location of the wire, the switch exhibiting a specified shape and size and operating in at least one of an on/off and a snooze/alarm mode.

The optional vibratory mode may operate as a wakeup device. Additional versions of the present device can also incorporate such features as an LED light and switch, as well as noise cancellation technology. A wireless version can also incorporate a remote transmitter associated with the clock radio or other input device, and which communicates with a receiver built into the sound generating device.

BRIEF DESCRIPTION OF THE DRAWINGS

Reference will now be made to the attached drawings, when read in combination with the following detailed description, wherein like reference numerals refer to like parts throughout the several views, and in which:

FIG. 2 is a cutaway view taken along line 2-2 of FIG. 1 and illustrating the pair of speakers incorporated into the pad according to the present invention;

FIG. 2A is a partial cutaway view of the flexible pad device based upon the variant of FIG. 2;

FIG. 2B is a partial view of a USB style plug capable of being substituted for the input jack shown in FIG. 2;

FIG. 2C is a partial view of a phone style mini-jack alternately substitutable with the input jack in FIG. 2;

FIG. 3 is a similar cutaway view showing a further variant of the present invention and by which the speakers are further recess mounted within the underlying pad;

FIG. 3A is a partial cutaway view of the flexible pad device of FIG. 3 and illustrating a variant representation by which a minimal cushioning material is provided upon the upper surface of the pad;

FIG. 4 is an illustration of an alternately configured sound generating device according to a further preferred embodiment and which illustrates a pair of substantially flattened and headphone style speakers sandwiched between upper soft perforated and lower rubberized layers of material and separated by a thin, bendable wire material about which is wrapped a soft material;

FIG. 4A is a partial cutaway view of the thin wire and soft interconnecting material illustrated in FIG. 4;

FIG. 5 is an exploded view illustrating a wireless variant according to the present invention and which includes a transmitter plugged into an audio output device, as well as a receiver (typically battery powered) which is connected to the speakers, typically placed under a pillow;

FIGS. 6A-6I illustrate a series of different configurations associated with the shaping of the sound generating device according to the present inventions;

FIG. 7 is a cutaway view of another alternate variant of the present invention and which illustrates a pair of vibration inducing components in substitution for the speakers illustrated in FIG. 2;

FIG. 7A is a partial view cutaway view illustrating a further variant incorporating an LED light and switch arrangement; and FIG. 8 is a diagrammatic view of a noise cancellation sound wave creating feature associated with the sound generating device according to any of the preferred embodiments.

DETAILED DESCRIPTION OF THE PREFERRED EMBODIMENTS

Figure 1:
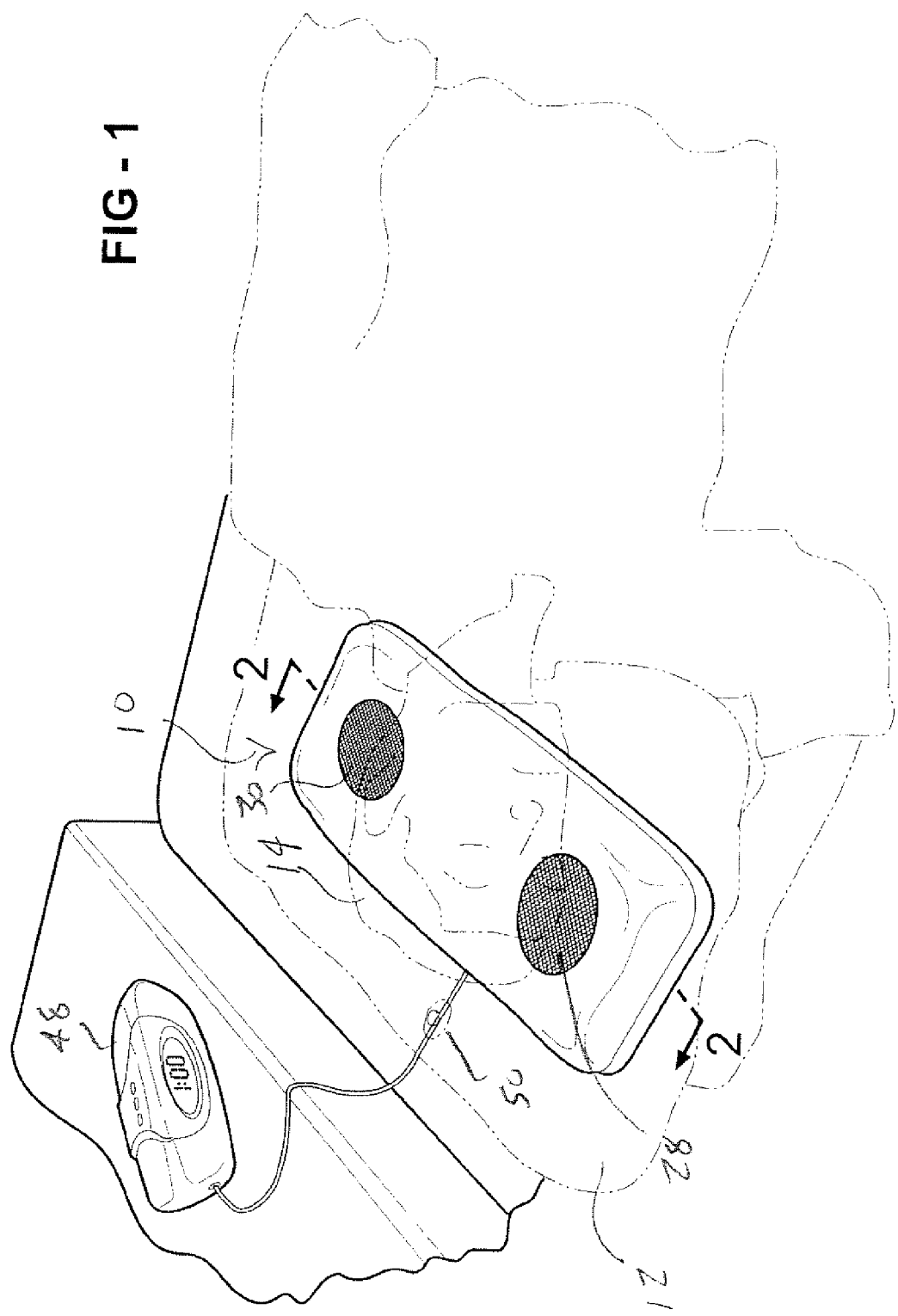
FIG. 1 is an environmental view of the speaker incorporated flexible pad in use with a pillow according to the present invention.

Referring now to FIG. 1, the present invention discloses at 10 a sound generating device which is an improvement over prior art devices, particularly in that it is incorporated into a small, relatively flat and flexible pad-like element which is capable of easily being inserted underneath an existing pillow (see in phantom at 12) or like cushion. As described previously, the advantage of pad-shaped sound generating component 10 is that it permits selective audible (e.g. music/alarm) output to a user 14 whose head is supported upon the pillow, and without disturbing a partner of the user.

As also described in the cutaway of FIG. 2 the invention exhibits a flexible three-dimensional and substantially planar shaped body exhibiting a specified thickness and having a specified shape and size including a soft interior 16 encased within a durable exterior covering 18. As will be discussed in subsequent embodiments, the padded body may include any varying amount of cushioning support, although certain preferred embodiments only contemplate the use of either minimal or no cushioning material located underneath the output speakers associated with the padded device 10. Additionally, and since the pad material is minimized in a preferred embodiment, a shape retaining metal wire is placed between the two speakers and encapsulated in material (as is subsequently referenced at 80 in FIG. 4A).

The use of an excessive amount of cushioning material within the pad device 10 has been found to render it unnecessarily bulky in use (such as placed under a pillow) and, as will be described in additional detail, the minimizing of the padding is desired in order that the device retain a slim profile, in use) with likewise thin profiled speakers, connecting wires and associated electronics as will also be discussed in additional detail. Additional features include the exterior covering 18 having a specified thickness and consistency and including at least one of a fabric and a rubberized material.

A pair of speakers 20 and 22 (see FIG. 2 cutaway) are arranged within apertured portions, at 24 and 26, respectively, defined in the body, and such that the speakers are arrayed in an upper facing direction relative to an associated upper surface of the substantially planar shaped body. The exterior covering incorporates a pair of audible permissive portions, see patches at 28 and 30, located over each of the speakers 20 and 22. The patches 28 and 30 are secured along their edges to adjoining edge locations of the exterior covering 18, see at 32 & 34 and 36 & 38, respectively in the cutaway of FIG. 2, the edges being supported upon a flattened rim portion associated with each of the speakers 20 and 22.

A wire 40 branches into two communicating subcomponents 42 and 44 and which connect to each of the speakers 20 and 22 for stereophonic sound (given that such wires are designed to carry different signals to each of the left and right speakers. The wire 40 extends from the body and terminates in an input jack 46 (or alternatively in a USB type plug shown at 46a, FIG. 2B for plugging into a computer hard-drive, IPod® or like digital output device, as well as a phone-style mini-jack 46b, FIG. 2C, as also shown) for connection to an external audio generating device, and such as referenced by tabletop radio 48 in FIG. 1. It is also envisioned that the input jack 46 can be attached to a stereo receiver/amplifier or the like, the selected piece of audio equipment typically providing the output wattage to the device 10. Additional embodiments also envision a wireless version of the present sound generating device (as will be further described), such not requiring a wire jack connection for issuing a desired audible output. Additional input connectors contemplate adapting the system for employing Blue Tooth® technology to communicating an audio output device to the speaker.

The variant illustrated in the partial cutaway of FIG. 2A illustrates at 49 a preferred variant of the present design and by which much of the cushioning material 16 (as shown in FIG. 2) is removed. In this variant, the degree and placement of cushioning material, see as further shown at 16', is modified such that the pad device slips more unobtrusively underneath a conventional pillow, thus reducing its degree of feel by a user's head resting upon the pillow.

In this manner, the cooperating placement of the soft foam inserts 16' and speakers 20 provide the padded body with a consistent thickness between first and second extending ends. As will be further discussed, the degree and placement of cushioning material within the pad device can be modified.

Referring further to the variant 10' of the device shown in FIG. 3, included are such additional features as an activate/deactivate switch 50 associated with an intermediate location of the wire 40. It is further envisioned that a microphone, battery, and associated circuitry can be incorporated in such a fashion as to play noise cancellation sound waves.

The switch 50 exhibits a specified shape and size and operates in at least one of an on/off and a snooze/alarm (as well as vibratory as will be discussed) mode as also referenced in the environmental view of FIG. 1. The remaining features are identically numbered in FIG. 3 for clarity in representation.

In use, the padded body is adapted to being placed underneath the existing pillow or cushion 12. The sound generating device is activated, such as by plugging into the radio or stereo component, to deliver an audio output, and which is selectively audible to the individual 14 whose head is supported upon the pillow or cushion. Given the partially muffling nature of the existing pillow, the audio output is substantially limited in its audible range to the user 14 and so that the output is not audible to a partner sleeping next to the user.

The thickness and consistency of the fabric covering, portions, see at 52 and 54 in FIG. 3, may also be increased to further modify the audible output characteristics of the device. Along these lines, a further modified variant of the present design (as set forth at 55 in FIG. 3A) contemplates the minimization of a padding material, see as shown at 58, placed between an upper surface of the speaker 20 and an inside face of a soft exterior layer 60.

The padding material 58 is located only along the top in this variant, a corresponding bottom edge of the variant 55 including only a rubberized material 62. Reference in FIG. 3A is particularly made to the manner in which the layers converge (see as shown at 64) to define a substantially flattened profile in a middle extending range of the padded support, it being further understood that a second speaker (not shown in FIG. 3B) is constructed in similar fashion as depicted. It should be further understood that the padded portion illustrated herein is, according to one preferred embodiment so minimized such that a shape retaining thin metal wire can be added or incorporated into the space between the left and right speakers and in order to maintain them in a consistently spaced apart fashion.

Referring now to FIG. 4, an illustration is shown at 66 of an alternately configured sound generating device according to a further preferred embodiment. The embodiment 66 illustrates a pair of substantially flattened and headphone style speakers, see at 68 and 70, sandwiched between upper soft perforated (at 72 and 74, respectively) and lower rubberized layers (see further at 76 and 78) of material.

The speakers 68 and 70 are separated by a thin, bendable wire material 80 (see also FIG. 4A) about which is wrapped a soft, typically fabric covered, material 82. An input jack is again shown, at 83, and extends from a selected speaker 70 for engagement with a headphone input jack associated with a remote located audio output device. The construction of the sound generating device 66 is otherwise functionally similar to that previously described in reference to the embodiment 10 in FIG. 1 and further permits the individual speakers 68 and 70 to be repositioned relative to one another and in order to achieve a desired configuration, such as when placed underneath a user's pillow.

Referring now to FIG. 5, an exploded view illustrates a wireless variant according to the present invention and which includes a transmitter 84 is plugged into the conventional audio output device 48. A receiver 86 is incorporated into a battery powered housing 88, and which may further be either connected to or incorporated (as shown) into a housing associated with a selected fabric ensconced speaker, see further at 90. The construction and operating characteristics of the wireless transmitter and receiver (i.e. such as frequency and range) are further such the receiver is easily capable of being communicated by the transmitter, at ranges of several feet or greater, and with the receiver located underneath a pillow or other cushioned article.

FIGS. 6A-6I illustrate a series of different configurations associated with the shaping of the sound generating device according to the present inventions. As will be described in further detail, such shapes and configurations may include a variety of different possibilities in which any number of speakers (or other sound, vibrational or light generating devices) are encased within a thin/narrow fabric material and which are again separated by an internally configured thin, bendable wire about which is wrapped a soft, typically fabric covering. The variants of FIGS. 6A-6I each further illustrate a wire connecting input jack, it again being understood that a wireless connection can be incorporated into any of the illustrated within the scope of the invention.

Addressing first FIG. 6A, a substantially linear extending body with opposite end located speakers is illustrated at 92. FIG. 6B shows it 94 a more crescent shape configuration including a plurality of four spaced apart speakers. As shown at 96 in FIG. 6C, a three sided and substantially "U" shaped configuration may employ a total of four speakers and, as further illustrated at 98 in FIG. 6D the connecting fabric material may exhibit a more flattened and arcuate outer profile.

Referencing FIG. 6E, at 100, a variation similar to that previously shown at 92 in FIG. 6A is illustrated, and by which the arcuate and flattened outer profile of FIG. 6D is employed in a two speaker arrangement. FIG. 6F illustrates at 107 a larger four speaker pair arrangement defined in a generally rectangular shape, within which a pair of interior cavities are defined to reduce fabric material content. FIG. 6G illustrates at 104 a generally profile flattened arcuate configuration (see again at 98 in FIG. 6D) employing a dual pair arrangement of speakers in a substantially square shape and with a single hollowed interior.

FIG. 6H shows, at 106, a variant of a single pair arrangement of speakers incorporated into a likewise profile flattened fabric material in linear extending fashion. Finally, example 108 in FIG. 6I illustrates a generally outer rounded and substantially triangular speaker configuration, again with a single open interior aperture. The understanding from the illustration of the several alternative variants of FIGS. 6A-6I, in cooperation with the several other embodiments illustrated herein, is that the sound generating device can incorporate virtually any two-dimensional profile and with any number of output devices located in a suitably dispersed fashion.

FIG. 7 is a cutaway view, at 110, of another alternate variant of the present invention and which illustrates a pair of vibration inducing components 112 and 114 in substitution for the speakers illustrated in FIG. 2. The components of FIG. 7 otherwise repeat those illustrated in FIG. 2, with the understanding that the ability to incorporate suitable and vibration inducing components 112 and 114 provides an alternative means for awakening an individual. It is also contemplated that suitably constructed or configured vibration components, in combination with speakers, can be employed within a single device and according to the invention.

Referring to FIG. 7A, a partial view cutaway view at 116 of a selected end-pad or cushioning, component illustrates a further variant incorporating an LED light 118 and (pressure activated) switch arrangement 120. As illustrated, a downward pressure force (see arrow 122) can act upon the switch 120 (or other suitable actuating arrangement) in order to contact an underside located battery (typically of a lithium type as shown at 124). This further occurs upon a selected gap 126 being closed as a result of the switch 120 closing the circuit with the battery 124 and to illuminate the LED 118. It is again understood that the LED can be employed cooperatively with or in substitution of the sound or vibration generating components illustrated throughout the several views of the present invention.

Referring finally to FIG. 8, a diagrammatic view is shown of a noise cancellation sound wave creating feature associated with the sound generating device for use in any of the preferred embodiments. In particular, a microphone 128 may receive an audio input, and which is communicated to a built in processor 130, this concurrently supplied by a battery or other power source 132.

The processor 130 in turn issues an output signal corresponding to a noise cancellation sound wave 134 and which operates as an anti-wave of sound to cancel ambient noise in the room. In practice, some calibration would be required, since the anti-wave is being played through a pillow, but it would be beneficial to some users.

In practice the present device provides a simplified and novel way to provide high quality sound. A myriad of existing audio output products it can connect to include such as clock radios, MP3 players, stereo systems, portable DVD players, hand held games, baby monitors, computers, televisions, cell phones, Blackberry®/Blackjack®/other small phones, sound soother devices and other noise machine devices.

Also, and since the present device combines the private listening capability of headphones with the comfort of not having to actually wear headphones, additional benefits achieved include better and more restful sleep, reduced conflicts between roommates/spouses, potential to wake up more slowly using a snooze feature without disturbing others, the ability to listen to music or other programming while falling asleep, the potential for one parent to wake up using a baby monitor while the other sleeps, privacy, as well as no discomfort associated with wearing headphones.

In one preferred application, the surrounding material employed is a 2 mm thick black nylon covered neoprene. While neoprene provides the features of a smooth top for comfort and a non-slip rubber bottom to maintain the location of the device, many other material options exist. Also, and while such as the nylon covering material comes in many standard colors, the same can be designed and produced in virtually any color or pattern. Additionally, such as the neoprene bottom also can be produced in several textures including smooth, textured, perforated, and Velcro® covered.

In addition to shape, color, materials, and connection type, there are features that could be incorporated into upgraded versions, these again include features such as volume control, snooze button, noise cancellation, white noise/soothing noise player, source switching, night light and vibration mode.

Having described my invention, other and additional preferred embodiments will become apparent to those skilled in the art to which it pertains.

The invention claimed is:

1. A sound generating device, comprising:
    an elongate body incorporating a bendable wire, said bendable wire further comprising at least a shape retaining wire and an electrically conducting wire; and
    an output generating component incorporated into said body and including a pair of flattened speakers mounted to opposite exposed ends of said bendable wire, said end mounted speakers being individually encased within a durable exterior covering associated with said body;
    said body adapted to being placed underneath an existing cushion with said speakers arranged in spaced apart fashion for delivering an audio output which is selectively audible to an individual whose head is supported upon the overlaying cushion.

2. The device as described in claim 1, further comprising said exterior covering having a specified thickness and consistency and further comprising at least one of an upper fabric layer and a lower rubberized material layer.

3. The device as described in claim 1, further comprising a wire communicating with said speakers, said wire extending from a selected one of said speakers and terminating in an input jack for connection to an external audible generating device.

4. The device as described in claim 3, further comprising an activate/deactivate switch associated with an intermediate location of said wire.

5. The device as described in claim 4, said switch exhibiting a specified shape and size and operating in at least one of an on/off and a snooze/alarm mode.

6. The device as described in claim 1, said output generating component further comprising a pair of vibrational inducing components arranged at locations within said body.

7. The device as described in claim 1, said output generating component further comprising an LED and switch arranged at locations associated with said body.

8. The device as described in claim 1, further comprising a microphone associated with said speakers for receiving an audio input and which is communicated to a built in and powered processor, said processor issuing an output signal corresponding to a noise cancellation sound wave and which operates as an anti-wave of sound to cancel ambient noise in a room.

9. The device as described in claim 1, further comprising a transmitter associated with an external audible generating device, a battery powered receiver incorporated into said body and communicating with said speakers to facilitate wireless communication with the external device.

* * * * *